US010420215B2

(12) United States Patent
Foo et al.

(10) Patent No.: US 10,420,215 B2
(45) Date of Patent: Sep. 17, 2019

(54) FLEXIBLE PRINTED CIRCUIT AND A METHOD OF FABRICATING A FLEXIBLE PRINTED CIRCUIT

(75) Inventors: Siang Sin Foo, Sin Ming Walk (SG); Choong Meng How, Choa Chu Kang Cresent (SG)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 164 days.

(21) Appl. No.: 14/396,964

(22) PCT Filed: Jun. 29, 2012

(86) PCT No.: PCT/US2012/044855
§ 371 (c)(1),
(2), (4) Date: Feb. 5, 2015

(87) PCT Pub. No.: WO2014/003779
PCT Pub. Date: Jan. 3, 2014

(65) Prior Publication Data
US 2015/0144381 A1    May 28, 2015

(51) Int. Cl.
*H05K 1/11* (2006.01)
*H05K 3/10* (2006.01)
(Continued)

(52) U.S. Cl.
CPC .............. *H05K 1/118* (2013.01); *H05K 3/10* (2013.01); *A61B 5/0408* (2013.01);
(Continued)

(58) Field of Classification Search
CPC .......... H05K 1/118; H05K 3/10; H05K 3/386; H05K 3/4092; H05K 2201/09127;
(Continued)

(56) References Cited

U.S. PATENT DOCUMENTS 2,964,587 A * 12/1960 Minot ................. H01B 7/0838
174/117 A
4,166,465 A * 9/1979 Esty ...................... A61B 18/16
606/32

(Continued)

FOREIGN PATENT DOCUMENTS

CN          101431863       5/2009
EP           2408279         1/2012
(Continued)

OTHER PUBLICATIONS

International Search Report for PCT International Application No. PCT/US2012/044855 dated Feb. 26, 2013, 3 pages.

*Primary Examiner* — Steven T Sawyer
*Assistant Examiner* — Paresh H Paghadal
(74) *Attorney, Agent, or Firm* — Clifton F. Richardson

(57) ABSTRACT

Various embodiments provide a flexible printed circuit comprising a substrate layer portion and an electrically-conductive layer portion. The electrically-conductive layer portion may be superimposed over the substrate layer portion. The substrate layer portion may have an opening formed therein and part of the electrically-conductive layer portion may be positioned over the opening to form a partially detachable tab. The tab may be for use in initiating separation of one portion of the flexible printed circuit from another portion of the flexible printed circuit. Various embodiments provide a corresponding method of fabrication of a flexible printed circuit. Various embodiments provide a corresponding method of fabrication of a plurality of electronic devices.

13 Claims, 5 Drawing Sheets

(51) Int. Cl.
    *A61B 5/0416*    (2006.01)
    *A61B 5/0408*    (2006.01)
    *H05K 3/38*      (2006.01)
    *H05K 3/40*      (2006.01)

(52) U.S. Cl.
    CPC ......... *A61B 5/0416* (2013.01); *A61B 5/04087* (2013.01); *H05K 3/386* (2013.01); *H05K 3/4092* (2013.01); *H05K 2201/09127* (2013.01); *Y10T 29/49155* (2015.01)

(58) Field of Classification Search
    CPC . A61B 5/04087; A61B 5/0408; A61B 5/0416; A61B 5/0492; A61B 5/0496; Y10T 29/49155
    See application file for complete search history.

(56) References Cited

U.S. PATENT DOCUMENTS

| | | | | |
|---|---|---|---|---|
| 4,674,512 A * | 6/1987 | Rolf | ................ | H01B 1/20 600/391 |
| 4,679,563 A * | 7/1987 | Wada | ................ | A61B 5/04087 600/391 |
| 4,922,911 A * | 5/1990 | Wada | ................ | A61B 5/04087 600/391 |
| 4,990,724 A * | 2/1991 | Suppelsa | ................ | H05K 1/118 174/261 |
| 5,288,539 A * | 2/1994 | Araki | ................ | H01L 23/4985 257/666 |
| 5,338,490 A * | 8/1994 | Dietz | ................ | A61B 5/04087 252/500 |
| 5,387,126 A * | 2/1995 | Austin | ................ | H05K 1/0293 174/254 |
| 5,457,149 A | 10/1995 | Hall | | |
| 5,640,763 A | 6/1997 | Lindberg | | |
| 5,868,671 A * | 2/1999 | Mahoney | ............ | A61B 5/04085 600/382 |
| 7,371,970 B2 | 5/2008 | Flammer et al. | | |
| 9,504,148 B1 * | 11/2016 | Hatch | ................ | H05K 1/02 |
| 9,510,762 B2 * | 12/2016 | Datovech | ............. | A61B 5/0478 |
| 2003/0130585 A1 * | 7/2003 | Wenger | ............. | A61B 5/04085 600/509 |
| 2006/0131260 A1 | 6/2006 | Okuyama | | |
| 2006/0291173 A1 | 12/2006 | Cho et al. | | |
| 2007/0032719 A1 * | 2/2007 | Menon | ................ | H01B 1/20 600/391 |
| 2010/0276183 A1 | 11/2010 | Ookawa | | |
| 2010/0321916 A1 | 12/2010 | Yoshida | | |
| 2011/0076522 A1 | 3/2011 | Hanazono | | |

FOREIGN PATENT DOCUMENTS

| | | |
|---|---|---|
| JP | 10-098081 | 4/1998 |
| JP | 2000-133891 | 5/2000 |
| JP | 2007-235067 | 9/2007 |
| JP | 2008-282850 | 11/2008 |
| KR | 2006-0134393 | 12/2006 |
| WO | 03/009658 | 1/2003 |

* cited by examiner

FLEXIBLE PRINTED CIRCUIT AND A METHOD OF FABRICATING A FLEXIBLE PRINTED CIRCUIT

TECHNICAL FIELD

Various embodiments relate to a flexible printed circuit and a method of fabricating a flexible printed circuit.

BACKGROUND

A flexible printed circuit (FPC) is a technology for providing electronic circuits on flexible substrates, such as, for example, polyimide, polyethylene naphthalate (PEN) or polyester film. For example, electronic components may be mounted on an FPC to provide a flexible electronic circuit board. Since an FPC is flexible, it may be useful in applications where electronics must bend for installation or assembly, or flex during normal use, such as, for example, in a folding cellular telephone.

SUMMARY

Various embodiments provide a flexible printed circuit comprising a substrate layer portion and an electrically-conductive layer portion, the electrically-conductive layer portion being superimposed over the substrate layer portion; wherein the substrate layer portion has an opening formed therein and part of the electrically-conductive layer portion is positioned over the opening to form a partially detachable tab, the tab being for use in initiating separation of one portion of the flexible printed circuit from another portion of the flexible printed circuit.

In an embodiment, the electrically-conductive layer portion comprises a groove, the groove being configured in use to guide the separation of said one portion from said other portion.

In an embodiment, the groove of the electrically-conductive layer portion is additionally configured in use to guide partial detachment of the tab from an adjacent part of the electrically-conductive layer portion.

In an embodiment, the flexible printed circuit further comprises a cover layer portion, the cover layer portion being superimposed over the electrically-conductive layer portion, the electrically-conductive layer portion being positioned in-between the cover layer portion and the substrate layer portion.

In an embodiment, the cover layer portion comprises a groove, the groove being configured in use to guide the separation of said one portion from said other portion.

In an embodiment, the groove of the cover layer portion is additionally configured in use to guide partial detachment of the tab from an adjacent part of the electrically conductive layer portion.

In an embodiment, the electrically-conductive layer portion comprises a notch adjacent to the opening of the substrate layer portion, the notch being for use in initiating partial detachment of the tab from an adjacent part of the electrically-conductive layer portion.

In an embodiment, said one portion and said other portion are adjacent strips of flexible printed circuit joined together along their respective length portions, wherein the tab is positioned at a first end portion of said one portion.

In an embodiment, a second tab is positioned at a second end portion of said one portion, the first and second end portions being at opposite ends of said one portion.

In an embodiment, said one portion comprises a discard portion of the flexible printed circuit.

In an embodiment, said other portion comprises an electric circuit.

Various embodiments provide a flexible printed circuit comprising a substrate layer portion and an electrically-conductive layer portion, the electrically-conductive layer portion being superimposed over the substrate layer portion; wherein the substrate layer portion has a plurality of openings formed therein and a different part of the electrically-conductive layer portion is positioned over each opening to form a plurality of partially detachable tabs, each tab being for use in initiating separation of two portions of the flexible printed circuit from each other. The further features stated above in respect of the above-mentioned flexible printed circuit are hereby restated in respect of the flexible printed circuit of this paragraph.

Various embodiments provide a method of fabricating a flexible printed circuit, the method comprising: forming an electrically-conductive layer portion over a substrate layer portion; and forming an opening in the substrate layer portion such that a part of the electrically-conductive layer portion is positioned over the opening to form a partially detachable tab, the tab being for use in initiating separation of one portion of the flexible printed circuit from another portion of the flexible printed circuit.

In an embodiment, the method further comprises forming a groove in the electrically-conductive layer portion, the groove being configured in use to guide the separation of said one portion from said other portion.

In an embodiment, the groove of the electrically-conductive layer portion is additionally configured in use to guide partial detachment of the tab from an adjacent part of the electrically conductive layer portion.

In an embodiment, the method further comprises forming a cover layer portion over the electrically-conductive layer portion so that the electrically-conductive layer portion is positioned in-between the cover layer portion and the substrate layer portion.

In an embodiment, the method further comprises forming a groove in the cover layer portion, the groove being configured in use to guide the separation of said one portion from said other portion.

In an embodiment, the groove of the cover layer portion is additionally configured in use to guide partial detachment of the tab from an adjacent part of the electrically conductive layer portion.

In an embodiment, the method further comprises forming a notch in the electrically-conductive layer portion adjacent to the opening of the substrate layer portion, the notch being for use in initiating partial detachment of the tab from an adjacent part of the electrically-conductive layer portion.

In an embodiment, said one portion and said other portion are formed as adjacent strips of flexible printed circuit joined together along their respective length portions, and wherein the tab is formed at a first end portion of said one portion.

In an embodiment, the method further comprises forming a second tab at a second end portion of said one portion, the first and second end portions being at opposite ends of said one portion.

In an embodiment, said one portion comprises a discard portion of the flexible printed circuit.

In an embodiment, said other portion comprises an electric circuit.

Various embodiments provide a method of fabricating a flexible printed circuit, the method comprising: forming an electrically-conductive layer portion over a substrate layer portion; and forming a plurality of openings in the substrate layer portion such that a different part of the electrically-conductive layer portion is positioned over each opening to form a plurality of partially detachable tabs, each tab being for use in initiating separation of two portions of the flexible printed circuit from each other. The further features stated above in respect of the above-mentioned method are hereby restated in respect of the method of this paragraph.

Various embodiments provide a method of fabricating a plurality of electronic devices, each electronic device comprising an electrical component coupled to a flexible printed circuit, the method comprising: coupling each of a plurality of electronic components to a flexible printed circuit, the flexible printed circuit comprising a substrate layer portion and an electrically-conductive layer portion, the electrically-conductive layer portion being superimposed over the substrate layer portion, wherein the substrate layer portion has a plurality of openings formed therein and a different part of the electrically-conductive layer portion is positioned over each opening to form a plurality of partially detachable tabs, each tab being for use in initiating separation of two portions of the flexible printed circuit from each other; and singularizing a plurality of portions of the flexible printed circuit using the plurality of partially detachable tabs, each different portion having coupled thereto a different one of the plurality of electronic components, to obtain a plurality of electronic devices. The further features stated above in respect of the above-mentioned flexible printed circuits are hereby restated in respect of the flexible printed circuit recited in the method of this paragraph.

BRIEF DESCRIPTION OF THE DRAWINGS

Embodiments of the invention will be better understood and readily apparent to one of ordinary skill in the art from the following written description, by way of example only, and in conjunction with the drawings, wherein like reference signs relate to like components, in which.

DETAILED DESCRIPTION

Figure 1:
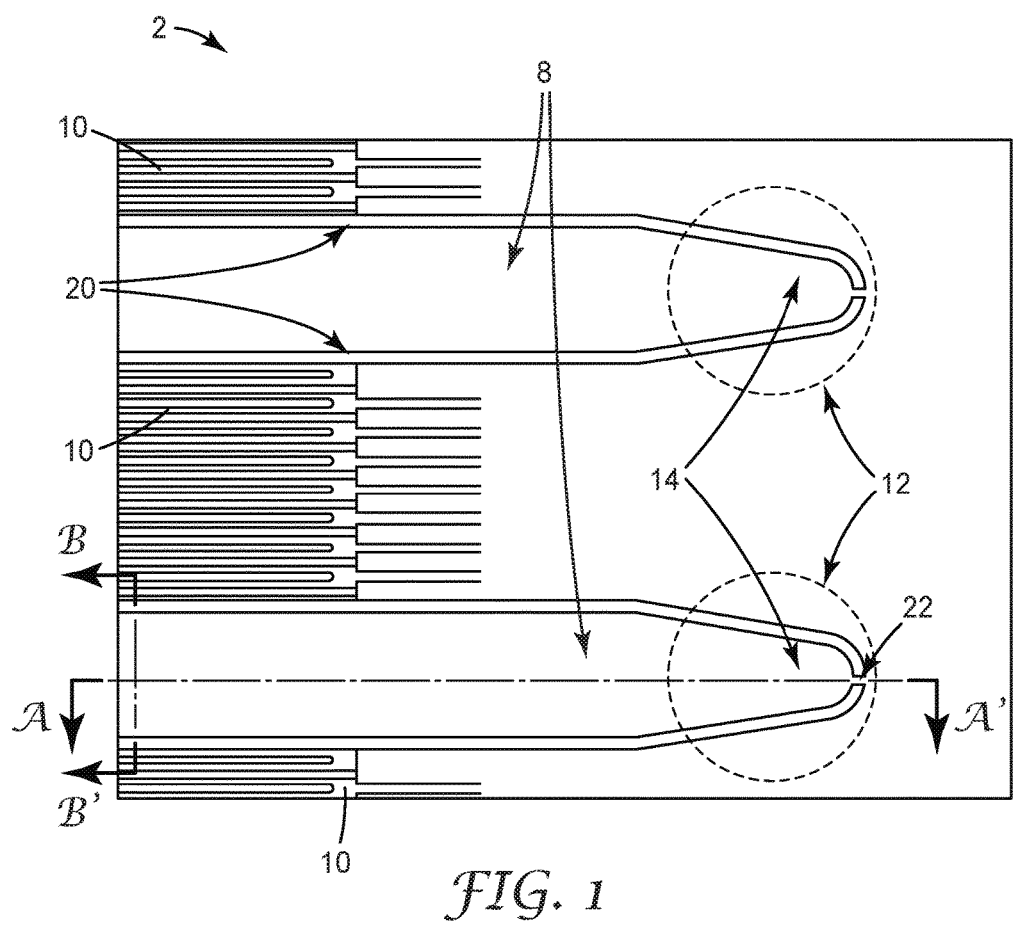
FIG. 1 is a top view of an FPC according to an embodiment.
Figure 2:
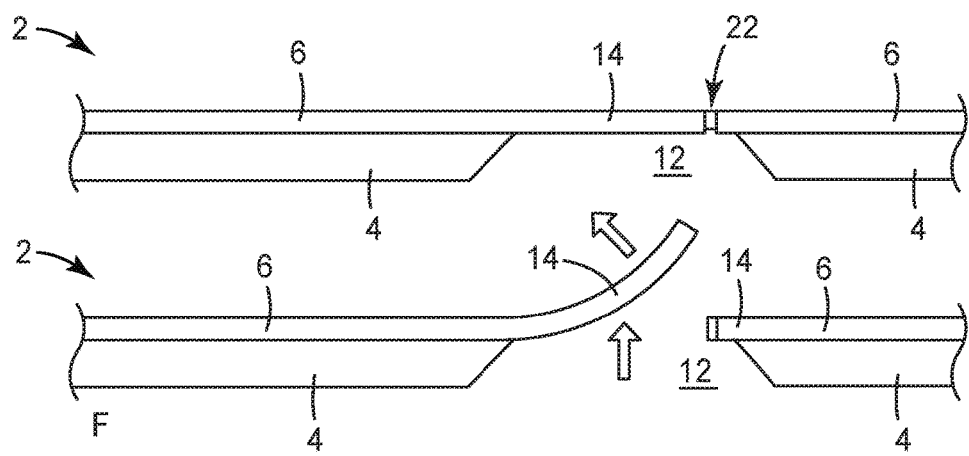
FIG. 2 is two cross-section views of the FPC of FIG. 1, both cross-sections corresponding to a line along AA' of FIG. 1.
Figure 3:
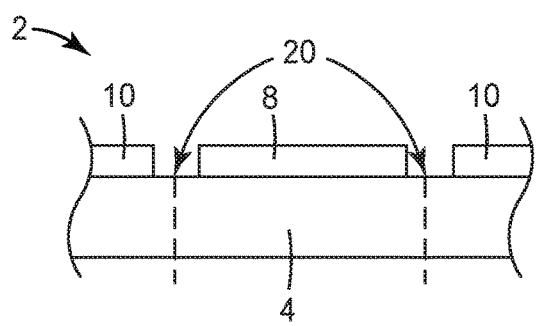
FIG. 3 is a cross-section view of the FPC of FIG. 1, the cross-section corresponding to a line along BB' of FIG. 1.

FIGS. 1, 2 and 3 illustrate an FPC 2 according to an embodiment. As seen more particularly on FIGS. 2A and 2B, in an embodiment, the FPC 2 comprises a substrate layer portion 4. In an embodiment, the substrate layer portion 4 is flexible. Additionally, in an embodiment, the FPC 2 comprises an electrically-conductive layer portion 6 superimposed over the substrate layer portion 4. Stated differently, the electrically-conductive layer portion 6 is positioned over the substrate layer portion 4, but not necessarily in direct contact therewith. In an embodiment, at least part of the electrically-conductive layer portion 6 may overhang at least part of the substrate layer portion 4, or visa versa, i.e. the two layer portions may not be perfectly aligned. In an embodiment, the FPC 2 is constructed or built by the superimposition of the electrically-conductive layer portion 6 over the substrate layer portion 4. In an embodiment, an adhesive layer portion (not shown) may be positioned in-between the substrate layer portion 4 and the electrically-conductive layer portion 6 to improve adherence of one layer portion to the other. In another embodiment, the electrically-conductive layer portion 6 is in direct contact with the substrate layer portion 4.

Various embodiments referenced herein are described in connection with various 'layer portions'. In some embodiments, it is to be understood that the term 'layer portion' is intended to include part of, but not all of, a layer of the FPC. However, in some other embodiments, it is to be understood that the term 'layer portion' is intended to include all of a layer of the FPC.

In an embodiment, as indicated by the solid lines of FIG. 1, parts of the electrically-conductive layer portion 6 are substantially free of electrically-conductive material so as to define one or more discard portions 8 of the FPC and one or more electric circuit portions 10 of the FPC. In an embodiment, a discard portion 8 is positioned in-between each pair of electric circuit portions 10, i.e. the discard portions 8 and the electric circuit portions 10 are positioned alternately.

In an embodiment, as indicated by the solid lines of FIG. 1, each electric circuit portion 10 comprises parts which are substantially free of electrically-conductive material so as to define one or more electrically-conductive traces for carrying an electric signal. Of course, the precise arrangement of electrically-conductive traces may vary between different embodiments and may depend on the intended electrical function of an electric circuit portion. In an embodiment, all electric circuit portions include the same arrangement of electrically-conductive traces; however, in another embodiment, each electric circuit portion includes a different arrangement of electrically-conductive traces to one or more other electric circuit portions.

In an embodiment, parts which are substantially free of electrically-conductive material may be absent of any material, i.e. no material may be superimposed over the substrate layer portion in that localised area. Accordingly, such parts may define channels or grooves in the electrically-conductive material which separate one or more electrically conductive traces for carrying electrical charge. In another embodiment, parts which are substantially free of electrically conductive material may have a reduced thickness of electrically conductive material, i.e. the electrically conductive material may be partially etched away. Accordingly, such partially etched portions may have a reduced charge carrying capability such that the partially etched portions separate one or more electrically conductive traces for carrying electrical charge. However, in another embodiment, parts which are substantially free of electrically-conductive material may comprise an alternative material, such as, for example, an electrically-insulating material. Accordingly, whilst the electrically-conductive layer portion 6 comprises parts which are electrically-conductive, the electrically-conductive layer portion 6 may also comprise parts which are electrically-insulating. Accordingly, the electrically-conductive layer portion 6 may define one or more separated electrically-conductive traces, rather than an electrically-conductive layer all of which is electrically conductive.

In an embodiment, the substrate layer portion comprises one or more openings 12. In FIG. 1, two openings 12 are indicated by circles having a broken line since, according to the orientation of the FPC 2 in FIG. 1, the openings 12 are positioned behind (i.e., beneath) the electrically-conductive layer portion 6 and so are shown in phantom. In an embodiment, the openings may have any shape, for example, a square-shape, a triangular shape or an irregular shape. As seen more particularly on FIG. 2, in an embodiment, a part of the electrically-conductive layer portion 6 is positioned over each opening to form a partially detachable tab 14. In an embodiment, the size and shape of the tab 14 is defined by the opening 12 and by the above-mentioned parts of the electrically-conductive layer which are substantially free of electrically-conductive material.

It is to be understood that in some embodiments, an FPC may comprise a single partially detachable tab 14. However, in some other embodiments, an FPC may comprise a plurality of partially detachable tabs 14.

In an embodiment, each tab 14 may be used for initiating separation of one portion of the FPC from another portion of the FPC. In an embodiment, each tab 14 may be associated (i.e. correspond) with two portions of the FPC 2, and each tab 14 may be used for initiating separation of the two associated portions from each other. In an embodiment, the association or correspondence may be based on which portions of the FPC are adjacent or proximate to the tab. For example, in the arrangement of FIG. 1, each tab 14 is configured in use to separate an discard portion 8 from an adjacent electric circuit portion 10. In an embodiment, to initiate separation, part of each tab 14 is detachable from an adjacent or surrounding part of the electrically-conductive layer portion 6. In an example, the tab 14 may be partially detached, i.e. part of the tab may be detached, by pushing or lifting the tab from either the substrate layer portion side or the electrically conductive layer portion side. In this way, it is possible to partially detach the tab 14 from a surrounding part of the electrically-conductive layer portion 6.

Figure 4:
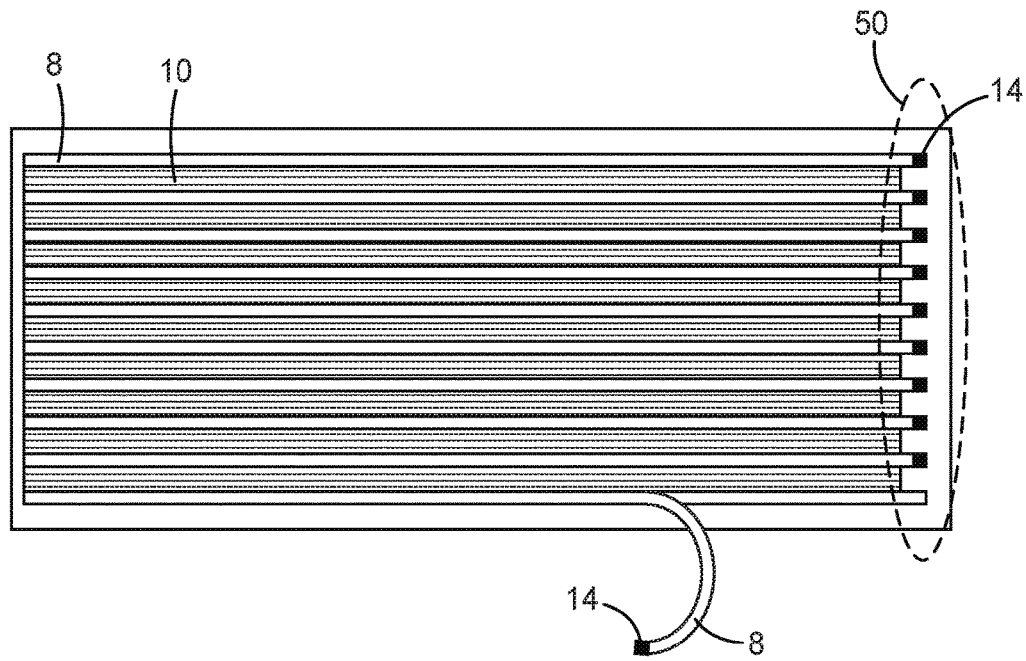
FIG. 4 is a top view illustrating the peeling-off of a portion of an FPC according to an embodiment.

In an embodiment, once the tab 14 is partially detached, the tab may be pulled or peeled to detach, separate or strip-off the discard portion 8 from the adjacent electric-circuit portion 10. In an embodiment, the peeling process may tear through at least part of the substrate layer portion 4. In an embodiment, the peeling process may tear through at least part of the electrically-conductive layer portion 6. This process is illustrated in the lower part of FIG. 2 and in FIG. 4. In this way, it is possible to separate an electric-circuit portion 10 from the remaining parts of the FPC 2. In an embodiment, the separated electric-circuit portion 10 may be used in the manufacture or use of an electric device, such as, for example, a cellular telephone, an endoscope (or catheter) employing ultrasound or optic fibre devices, or a light-emitting diode television.

In an embodiment, at least part of the electrically-conductive layer portion 6 which is free of electrically-conductive material specifically defines a groove 20. The groove 20 is configured in use to guide a path of separation initiated by peeling the tab 14. Accordingly, the path of separation can be guided such that it does not tear through some or all of the electric-circuit portion 10. Therefore, the electric functionality of the electric-circuit portion can be preserved and damage thereto can be avoided. In an embodiment, the path of separation may also be guided by an edge of the discard portion 8 and/or the electric-circuit portion 10. For example, the discard portion 8 and/or the electric-circuit portion 10 may comprise an electrically conductive layer portion 6 comprising copper, and the physical properties of the copper may resist tearing thereby further guiding the path of separation.

As seen in FIG. 1, in an embodiment, the groove 20 defines a complete outline of the discard portion 8. Accordingly, the precise shape of the discard portion 8 which is peeled off can be accurately controlled by the groove 20. In another embodiment, the groove 20 defines only a portion of the complete outline of the discard portion. In yet another embodiment, the groove 20 may define a complete, broken outline or only a partial, broken outline of the discard portion 8. Accordingly, the structural integrity of the FPC 2 whilst in an unstripped or unpeeled state may be preserved, i.e. accidental peeling may be avoided. Regardless of the precise configuration of the groove 20, when the tab 14 is pulled, the discard portion 8 peels away from an adjacent electric circuit portion 10 along a line of separation guided by the groove 20.

In an embodiment, the groove 20 extends through the whole thickness of the electrically-conductive layer portion. Accordingly, the path of separation may be guided accurately. In another embodiment, the groove 20 extends through only part of the thickness of the electrically-conductive layer portion. In yet another embodiment, the groove thickness may vary along its length and/or width.

In an embodiment, a notch 22 may be formed in the electrically-conductive layer portion 6 adjacent to an opening 12 in the substrate layer portion 4. The notch 22 may comprise a part of the electrically-conductive layer portion 6 at which the thickness is reduced compared to a majority of the remainder of the electrically-conductive layer portion 6. In an embodiment, the notch 22 may be made by providing a depression in either or both surfaces of the electrically-conductive layer portion 6. In another embodiment, the notch may be a narrow incision in the electrically conducive layer around the tab. Accordingly, the notch 22 may provide a localised area of weakness to facilitate and initiate partial detachment of the tab 14 from an adjacent part of the electrically-conductive layer portion 6. In an embodiment, a notch 22 is provided for each tab 14.

Figure 5:
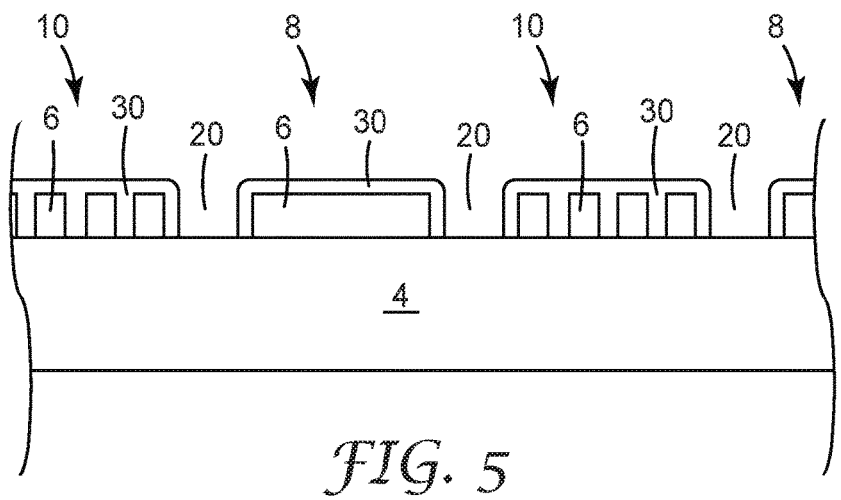
FIG. 5 is a magnified view of the FPC of FIG. 3 according to an embodiment.

As seen in FIG. 5, the FPC may additionally comprise a cover layer portion 30 positioned over the electrically-conductive layer portion 6. In an embodiment, the cover layer portion is formed directly over at least the electrically conductive layer portion 6. In an embodiment where gaps are present in the electrically-conductive layer portion 6, the cover layer portion 30 may bridge those gaps and may contact a layer portion positioned below the electrically-conductive layer portion 6, such as, for example, the substrate layer portion 4. The cover layer portion 30 may provide physical protection for layer portions of the FPC 2 which are positioned below it. The cover layer portion 30 may also improve the structural integrity of the FPC, whilst still permitting flex. In an embodiment, the cover layer portion 30 may be positioned over the complete area of the electrically-conductive layer portion 6. However, in another embodiment, the cover layer portion 30 may be positioned over only a part or parts of the complete area. In an embodiment, an adhesive layer may be positioned under the cover layer portion 30 to help it adhere to the layer portion below. In an embodiment, no adhesive layer may be positioned between the cover layer portion 30 and the electrically-conductive layer portion 6, i.e. the cover layer portion 30 may bond directly to the electrically-conductive layer portion 6 without the need for a separate adhesive layer.

In an embodiment, the above-described groove 20 may also be present in the cover layer portion 30. In an embodiment, the groove extends through the whole thickness of the cover layer portion 30. However, in another embodiment, the cover layer portion 30 may be positioned over the groove 20 and at least partly filling it in. In another embodiment, the groove 20 may be present in the cover layer portion 30 only, i.e. the groove may not be present in the electrically-conductive layer portion 6.

In an embodiment, the above-described notch 22 may also be present in the cover layer portion 30. However, in another embodiment, the cover layer portion may be positioned over the notch 22 and at least partly filling it in. In another embodiment, the notch 22 may be present in the cover layer portion 30 only, i.e. the notch 22 may not be present in the electrically-conductive layer portion 6.

In an embodiment, the substrate layer portion 4 provides a flexible layer on which the electrically-conductive layer portion 6 is positioned. In an embodiment, the electrically-conductive layer portion 6 provides an electric circuit portion 10. Accordingly, the FPC 2 may provide a flexible electric circuit which can flex during normal use.

In an embodiment, the FPC 2, the electric circuit portion 10 and the discard portion 8 may be arranged with any shape. As seen more particularly on FIG. 4, in the illustrated embodiments, the FPC comprises a substantially rectangular sheet, wherein the sheet may be rolled onto a roller. Further, each electric circuit portion 10 may comprise a strip form and many electric circuit portions 10 may be arranged side-by-side and in a row on the rectangular sheet. Accordingly, the discard portions 8 also comprise a strip form such that adjacent electric circuit portions can be separated from the rectangular sheet with a minimum of wastage, i.e. the discard portions may be thinner that the electric circuit portions. According to the above configuration of the FPC 2, a tab 14 may be located at one end portion of each discard portion strip, as indicate in FIG. 4 at region 50. However, in another embodiment, a tab may be located at each opposite end portion of the strip. Accordingly, the discard portion may be stripped off starting from either end. Therefore, use of the FPC may be simplified.

In an embodiment, the substrate layer portion may comprise a flexible electrically insulating (dielectric) material, such as, for example, polyimide (PI), transparent conductive polyester film, polyether ether ketone (PEEK), polyester (PET), polyethylene napthalate (PEN), polyetherimide (PEI), along with various fluropolymers (FEP) and polyimide copolymer films. In an embodiment, the electrically-conductive layer portion may comprise an electrically conductive material, such as, for example, metal. In an embodiment, the metal may comprise copper. In an embodiment, the electrically conductive material may comprise a metal filled conductive polymer. In an embodiment, where an adhesive layer is present between the substrate layer portion and the electrically-conductive layer portion, and/or between the cover layer portion and a layer portion below, such adhesive layer may comprise epoxy.

In an embodiment, the substrate layer portion may have a thickness of between about 1.0 mm and about 2.0 mm, but preferably about 1.5 mm. In an embodiment, the electrically-conductive layer portion may have a thickness of between about 10.0 µm and about 35.0 µm, but preferably about 22.5 µm. In an embodiment, the cover layer portion may have a thickness of between about 15.0 µm and about 50.0 µm, but preferably about 32.5 µm.

In an embodiment, the tab 14 can be pushed or peeled to separate it from a main plane of the electrically-conductive layer portion 6. Subsequently, a strip or rail (i.e. an discard portion 8) connected to the tab 14 may be peeled-off from a wanted strip (i.e. an electric circuit portion 10).

According to the above, an embodiment provides an integral tab to initiate peeling-/stripping-/tearing-off of part of an FPC for separation of an individual flexible printed circuit strip, i.e. an individual electric circuit portion 10. In an embodiment, the tab is defined by a copper feature over an opening in a polyimide base or substrate layer portion. In an embodiment, the copper feature is continuous with the stripped-off rail (discard portion 8) and can be used to separate an individual electric circuit portion 10 from the FPC 2.

In an embodiment, the tab is designed in the artwork of the FPC to simplify manufacture of the tab.

In the above-described embodiments, each opening 12 is substantially circular. However, in another embodiment, the shape and/or size of each opening 12 may be varied to provide a tab 14 of different shape and/or size. In an embodiment, the shape and/or size of each opening 12 may be substantially the same so that all tabs 14 are substantially the same shape and/or size. However, in another embodiment, one or more openings 12 may have a different shape and/or size from one or more other openings 12 so that some or all of the tabs 14 are different. In yet another embodiment, one or more openings 12 may be sized and shaped in order to suit long flexible circuit designs and/or cater to automated peeling machines. For example, an automated peeling machine may be a machine configured in use to mechanically peel off an discard portion from a FPC in order to obtain an electric circuit portion for use in electronic device operation or manufacture.

Figure 6:
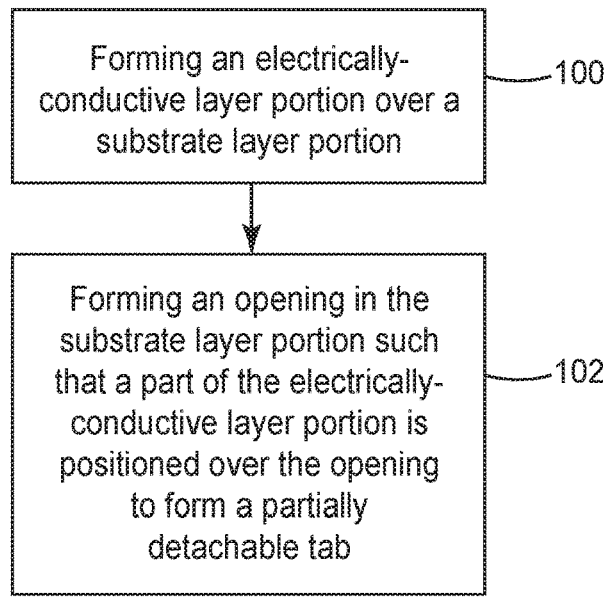
FIG. 6 is a flow diagram illustrating a method of fabricating an FPC according to an embodiment.

FIG. 6 illustrates an exemplary method for manufacturing an FPC 2 according to an embodiment. At 100, an electrically-conductive layer portion 6 is formed over a substrate layer portion 4. At 102, an opening 12 in the substrate layer portion 4 is formed such that a part of the electrically-conductive layer portion 6 is positioned over the opening 12 to form a partially detachable tab 14. As mentioned above, the tab 14 may be for use in initiating separation of one portion 8 of the FPC 2 from another portion 10 of the FPC 2.

Figure 7:
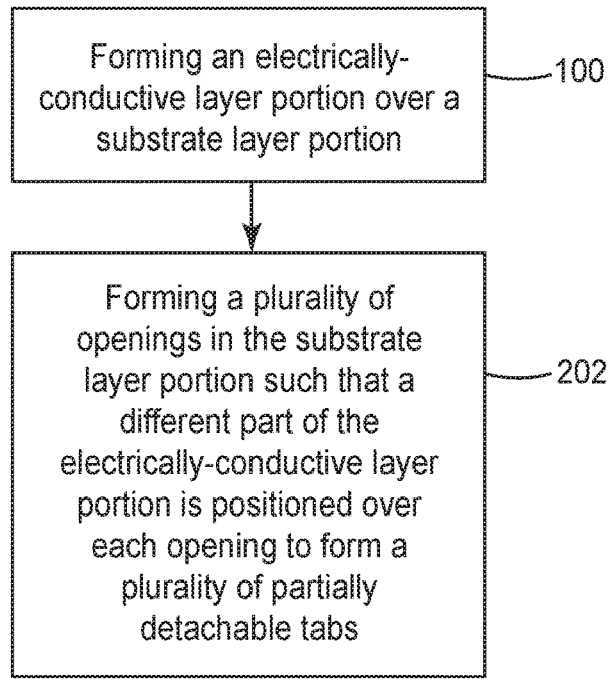
FIG. 7 is a flow diagram illustrating a method of fabricating an FPC according to another embodiment.

FIG. 7 illustrates an exemplary method for manufacturing an FPC according to another embodiment. As before, at 100, an electrically-conductive layer portion 6 is formed over a substrate layer portion 4. However, at 202, a plurality of openings 12 in the substrate layer portion 4 is formed such that a different part of the electrically-conductive layer portion 6 is positioned over each opening 12 to form a plurality of partially detachable tabs 14. As mentioned above, each tab 14 may be for use in initiating separation of two portions (8 and 10) of the FPC 2 from each other.

In an embodiment, the electrically-conductive layer portion 6 is formed on the substrate layer portion 4 using a photolithographic process. In an embodiment, an adhesive layer may be positioned in-between the electrically-conductive layer 6 and the substrate layer portion 4 to help the two layers adhere to each other. In another embodiment, the electrically-conductive layer portion 6 may be formed directly over the substrate layer portion 4, i.e. without an intervening adhesive layer. In an embodiment, the parts of the electrically-conductive layer portion 6 which are free of electrically-conductive material are formed using chemical etching. Stated differently, the electrically-conductive traces may be formed using a subtractive process, wherein a solid block of electrically-conductive material is first laid down then portions are etched away to form traces. However, in some other embodiments, the electrically-conductive traces may be formed using an additive process, wherein traces are grown up from the substrate layer portion.

In an embodiment, the above-described cover layer portion is laminated over the electrically-conductive layer portion using a photolithographic process. In an embodiment, the cover layer portion is formed using a dry film solder mask. In another embodiment, the cover layer portion is formed using a screen printing process.

In an embodiment, the FPC may be fabricated using a curing method.

In an embodiment wherein each electric circuit portion comprises a strip, the strip may consist of lengths between about 0.5 m and about 2.0 m, and widths as small as about 2.0 mm. In an embodiment in which the FPC is manufactured in a roll format, the roll may comprise a width of about 300.0 mm and each electric circuit portion may comprise a strip having a width of about 100.0 mm or less depending of the design of the circuit.

For example, eighteen individual strips having a width of about 2.0 mm may be designed on a delivery reel having a width of about 70.0 mm. In an embodiment, separating the roll into eighteen individual electric circuit portion strips may be done by using the above-mentioned tabs to peel or strip away the discard portion strips in-between the electric circuit portion strips. The peeling process will tear away the base polyimide film and may be guided by grooves defined by the electrically-conductive layer portion and/or the cover layer portion.

In the above-described embodiments, a single FPC comprises more than one tab. However, it is to be understood that in some other embodiments, a single FPC may comprise only a single tab. Furthermore, it is to be understood that in some further embodiments, the FPC may comprise any number of tabs, such as, for example, one tab per discard portion, two tabs per discard portion, three tabs per discard portion, etc. Furthermore, the precise location of the or each tab may vary, for example, in dependence on an intended use.

In an embodiment, the flexible printed circuit (FPC) is a laminate. Stated differently, the FPC may be constructed from 2, 3, 4 or more layer portions or layers of material bonded together.

Figure 8:
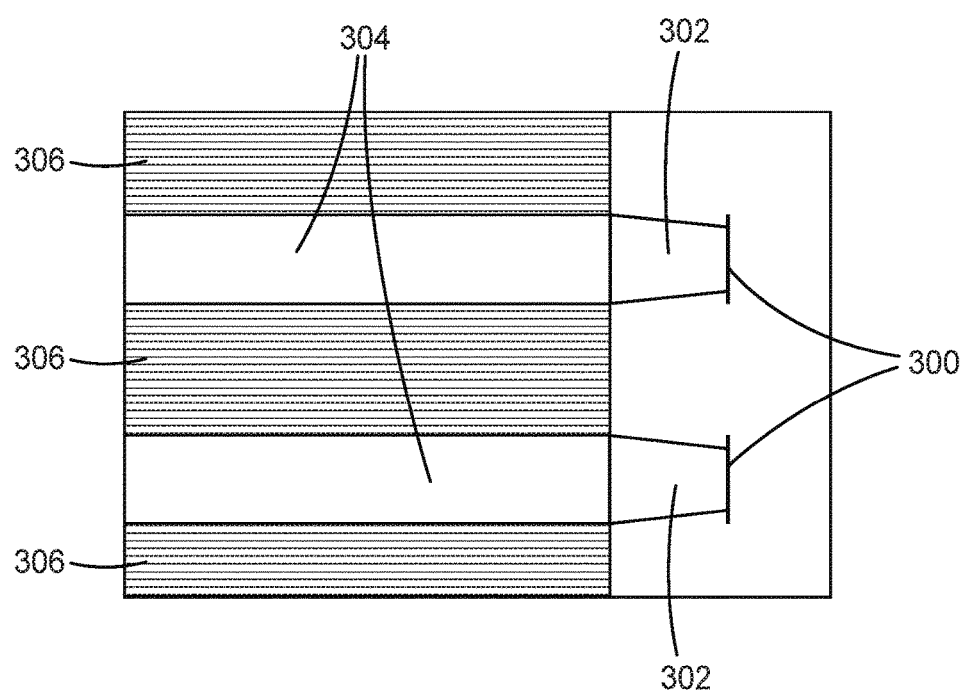
FIG. 8 is a top view of an FPC according to a known prior art arrangement.

It is an advantage of the above-described embodiments that it is not necessary to initiate the peeling process by manually making cuts in the FPC to produce flaps. FIG. 8 illustrates this manual method of making cuts 300 in the FPC to produce flaps 302. The flaps 302 may be used to separate discard portions 304 of the FPC from wanted portions 306, i.e. electric circuit portions. Accordingly, an advantage of the above-described embodiments is that separation of an individual electric circuit portion is made easier compared to the method illustrated in FIG. 8. Consequently, the process of separating an individual electric circuit portion is made faster compared to the method illustrated in FIG. 8.

It is an advantage of the above-described embodiments that no punch tool is required to make manual cuts in the FPC to produce flaps. It is noted that a punch tool may be a tool configured in use to generate the manual cuts 300 of FIG. 8. Accordingly, an advantage of the above-described embodiments is that machine and tooling investment can be avoided. Further, since the punch tool will operate with a certain cutting tolerance, it is an advantage of the above-described embodiments that portions of the FPC are not spoiled as a result of misalignment of the punch tool with the FPC. Furthermore, since no punch tool is required, it is an advantage of the above-described embodiments that the electric circuit portions may be positioned closer together, i.e. the discard portions may be made smaller. Stated differently, when using a punching tool, discard portions must comprise a larger size compared to discard portions which comprise a tab in accordance with an embodiment. Accordingly, an advantage of the above-described embodiments is that the number of electric circuit portions for a given area of FPC may be increased.

Various embodiments may solve the problem of having to form manually cut flaps to strip-off or peel-off discard portions, as this problem can create unnecessary process and costs. Furthermore manually cutting flaps can cause damage to the electric circuit portions, for example, as a result of machine tolerances or human error.

An advantage of the above-described embodiments is that, since no punching tool is required, automating the process of stripping-off or peeling-off discard strips to separate electric circuit portions may be simplified.

In an embodiment, an FPC sheet comprising a row of electric circuit portion strips alternately arranged with a row of discard portion strips may be used to mass-produce a plurality of electronic devices. In an embodiment, each electronic device may comprise a portion (e.g. an electric circuit portion) of the FPC sheet coupled to an electronic component. For example, the electronic component may be an electrical connector, a transducer, a camera, or a healthcare related component, such as, an ultrasound transducer.

The FPC may be as described above. For example, the FPC may comprise a substrate layer portion and an electrically-conductive layer portion. The electrically-conductive layer portion may be superimposed over the substrate layer portion. The substrate layer portion may have a plurality of openings formed therein and a different part of the electrically-conductive layer portion may be positioned over each opening to form a plurality of partially detachable tabs. Each tab may be for use in initiating separation of two portions of the FPC from each other. The FPC may comprise a row of electric circuit portions arranged alternatively with a row of discard portions.

In an embodiment, the plurality of electronic components may be arranged in a row. For example, the plurality of electronic components may be contained within a holder configured in use to arrange the components in a row. Alternatively, the electronic components may be detachably attached to each other in a row. Accordingly, each component of the row of components may be aligned with a different one of the electric circuit portions of the FPC sheet. In this way, coupling of each component to a respective electric circuit portion strip may be simplified, for example, to ease mass-production of a plurality of electronic devices.

In an embodiment, once each of the plurality of electronic components is coupled to a respective portion (e.g. electric circuit portion) of the FPC sheet, each of the plurality of detachable tabs is peeled. In an embodiment, each of the plurality of tabs is partially detached before the peeling operation. In an embodiment, detachment of all tabs may be performed in a single operation. In an embodiment, peeling of all tabs may be performed in a single operation. In this way, a plurality of electric circuit portions of the FPC may be singularized at once, wherein each different portion has coupled thereto a different one of the plurality of electronic components. By singularize, it is meant that the electronic circuit portion having an electronic component attached thereto is completely detached from all other portions (i.e. all discard portions and all other electric circuit portions) of the FPC sheet. Accordingly, it may be possible to obtain in one operation a plurality of electronic devices, wherein each electronic device comprises an electronic component coupled to a FPC.

In an embodiment, a tool may be provided which is configured in use to detach and/or pull (i.e. peel) each tab at once in order to singularize the plurality of electronic devices in one operation. In an embodiment, a master tab may be provided which is configured in use to operate as an above-mentioned tab; however, pulling (i.e. peeling) the master tab may cause the peeling of all other tabs together, i.e. in one operation. For example, the master tab may be physically connected to each of the plurality of tabs such that peeling the master tab initiates peeling of each of the plurality of tabs. For example, the master tab may be defined in the same way as described above in respect of the above-mentioned tab, i.e. it may be defined in the artwork of the FPC.

According to the above embodiments, mass production of a plurality of electrical devices may be facilitated using embodiments of the above-described FPC.

In an embodiment, an electric circuit portion which has been stripped off using an above-mentioned tab may be used in a variety of different applications. In a first example, the electric circuit portion has a strip form and is used in the construction of a medical endoscope. Specifically, one or a number of electric circuit portion strips may be housed lengthways within a tube, such as, for example, a flexible tube. The or each electric circuit portion may be longer than the tube and may protrude from either or both ends of the tube. At one end, the or each electric circuit portion may be coupled either to an electrical connector for subsequent connection to a detector, or directly to a detector, such as, for example, an ultrasound transducer or a camera. At the other end, each electric circuit portion may be coupled to a computing device. For example, the computing device may be configured in use to receive, process and/or transmit data obtained from the detector via the or each electric circuit portion. Accordingly, the medical endoscope may be introduced inside a patient in order to detect and/or measure a biological parameter. Furthermore, in order that the electric circuit portion is capable of withstanding sterilization, such as, heat and/or chemical sterilization, the electric circuit portion may additionally comprise an outer heat tolerant layer portion or an outer chemically inert layer portion. In view of the above, in an embodiment, the FPC 2 may additionally comprise an outer heat tolerant layer portion and/or an outer chemically inert layer portion.

In a second example, the electric circuit portion may comprise one or more component connection pads. For example, the or each component connection pad may be defined by the electrically-conductive traces of the electric circuit portion. In an embodiment, each component connection pad comprises an area of electrically-conductive material which is sized and shaped to be coupled to a terminal of an electronic component. For example, the electronic component may be an LED, and each component connection pad may be configured in use to be coupled (e.g. soldered) to a terminal of an LED. Accordingly, the electric circuit portion may be used to create a strip of LEDs. In an example, the strip of LEDs may be used in the construction of an LED display device, such as, an LED television.

An advantage of an individual electric circuit portion which has been separated from an FPC in accordance with an embodiment is that it may provide a replacement to a wire or cable solution. Specifically, as the density of wires and cables in electronic packaging increases, for example, due to reductions in packaging volume, it becomes harder and harder to find space for cables or wires, especially if the wires and cables need to be placed in devices having long, narrow passages, such as endoscopic catheters. However, individual electric circuit portions can be advantageous since they can be made smaller than wires and cables. Therefore, individual electronic circuit portions can be used to replace wires and cables.

Additionally, wires and cables require connectors in order to couple then to electric components. These connectors also require space and compound the problem mentioned above. In an embodiment, an electric circuit portion of the FPC may provide further advantages since the need for connectors can be eliminated by coupling electronic components directly to the electrically-conductive traces of the electric circuit portion.

It will be appreciated by a person skilled in the art that numerous variations and/or modifications may be made to one or more of the above-described embodiments without departing from the spirit or scope of the invention as broadly described in the appended claims. The above-described embodiments are, therefore, to be considered in all respects to be illustrative and not restrictive.

The invention claimed is:

1. A flexible printed circuit comprising a substrate layer portion and an electrically-conductive layer portion, the electrically-conductive layer portion being superimposed over the substrate layer portion;
wherein the substrate layer portion has an opening formed therein and part of the electrically-conductive layer portion is positioned over the opening to form a detachable tab, the tab being for use in initiating separation of one portion of the flexible printed circuit from another portion of the flexible printed circuit, said another portion comprising at least one electric circuit, the at least one electric circuit comprising a plurality of electrically conductive traces,
wherein the electrically-conductive layer portion comprises a notch adjacent to and over the opening of the substrate layer portion, the notch connecting the tab to an adjacent part of the electrically-conductive layer portion, the notch providing a localized area of weakness in the electrically-conductive layer portion and being for use in initiating detachment of the tab from the adjacent part of the electrically-conductive layer portion, and
wherein the flexible printed circuit is configured such that said one portion is completely detachable from said another portion without damaging the at least one electric circuit by peeling the tab, said one portion comprising the tab.

2. The flexible printed circuit of claim 1, wherein the electrically-conductive layer portion comprises a groove, the groove being configured in use to guide the separation of said one portion from said another portion.

3. The flexible printed circuit of claim 2, wherein the groove of the electrically-conductive layer portion is additionally configured in use to guide partial detachment of the tab from an adjacent part of the electrically-conductive layer portion.

4. The flexible printed circuit of claim 1, wherein the flexible printed circuit further comprises a cover layer portion, the cover layer portion being superimposed over the electrically-conductive layer portion, the electrically-conductive layer portion being positioned in-between the cover layer portion and the substrate layer portion.

5. The flexible printed circuit of claim 4, wherein the cover layer portion comprises a groove, the groove being configured in use to guide the separation of said one portion from said another portion.

6. The flexible printed circuit of claim 5, wherein the groove of the cover layer portion is additionally configured in use to guide partial detachment of the tab from an adjacent part of the electrically conductive layer portion.

7. The flexible printed circuit of claim 1, wherein said one portion and said another portion are adjacent strips of flexible printed circuit joined together along their respective length portions, wherein the tab is positioned at a first end portion of said one portion.

8. The flexible printed circuit of claim 7, wherein a second tab is positioned at a second end portion of said one portion, the first and second end portions being at opposite ends of said one portion.

9. A flexible printed circuit comprising a substrate layer portion and an electrically-conductive layer portion, the electrically-conductive layer portion being superimposed over the substrate layer portion;
wherein the substrate layer portion has a plurality of openings formed therein and a different part of the electrically-conductive layer portion is positioned over each opening to form a plurality of detachable tabs, each tab being for use in initiating separation of two portions of the flexible printed circuit from each other, one of the two portions comprising the tab, the other of the two portions comprising an electric circuit, the electric circuit comprising a plurality of electrically conductive traces, said one portion being completely detachable from said other portion without damaging the electric circuit by peeling the tab, and
wherein for each tab in the plurality of detachable tabs, the electrically-conductive layer portion comprises a notch adjacent to and over the opening of the substrate layer portion, the notch connecting the tab to an adjacent part of the electrically-conductive layer portion, the notch providing a localized area of weakness in the electrically-conductive layer portion and being for use in initiating detachment of the tab from the adjacent part of the electrically-conductive layer portion.

10. A flexible printed circuit comprising a substrate layer portion and an electrically-conductive layer portion disposed on the substrate layer portion, the electrically-conductive layer portion comprising a plurality of alternating electric circuit portions and discard portions, each of the discard portions comprising a partially detachable tab disposed over an opening in the substrate layer portion, and wherein for each tab in the plurality of discard portions, the electrically-conductive layer portion comprising a notch adjacent to and over the opening of the substrate layer portion, the notch connecting the tab to an adjacent part of the electrically-conductive layer portion, the notch providing a localized area of weakness in the electrically-conductive layer portion and being for use in initiating detachment of the tab from the adjacent part of the electrically-conductive layer portion, each of the discard portions being separated from an adjacent electric circuit portion by a groove in the electrically-conductive layer portion, each electric circuit portion comprising a plurality of electrically conductive traces.

11. The flexible printed circuit of claim 10, wherein the discard portions are arranged in parallel rows.

12. The flexible printed circuit of claim 10, wherein each electric circuit portion comprises a same arrangement of the electrically conductive traces.

13. The flexible printed circuit of claim 10, wherein the flexible printed circuit further comprises a cover layer portion disposed on the electrically-conductive layer portion opposite the substrate layer portion.

* * * * *